(12) United States Patent
Izumi et al.

(10) Patent No.: US 7,031,134 B2
(45) Date of Patent: Apr. 18, 2006

(54) DISPLAY DEVICE INCLUDING ION GENERATOR AND ELECTRONIC APPLIANCE

(75) Inventors: Yoshihiro Izumi, Kashihara (JP); Yasukuni Yamane, Nara (JP)

(73) Assignee: Sharp Kabushiki Kaisha, Osaka (JP)

( * ) Notice: Subject to any disclaimer, the term of this patent is extended or adjusted under 35 U.S.C. 154(b) by 227 days.

(21) Appl. No.: 10/348,763

(22) Filed: Jan. 23, 2003

(65) Prior Publication Data

US 2003/0137794 A1 Jul. 24, 2003

(30) Foreign Application Priority Data

Jan. 23, 2002 (JP) ............................. 2002-013736
Oct. 3, 2002 (JP) ............................. 2002-290678

(51) Int. Cl.
*H02H 1/00* (2006.01)
(52) U.S. Cl. .................................................... 361/231
(58) Field of Classification Search ................ 361/212, 361/230, 231; 96/60
See application file for complete search history.

(56) References Cited

U.S. PATENT DOCUMENTS

| | | | |
|---|---|---|---|
| 4,692,779 A | | 9/1987 | Ando et al. |
| 4,757,422 A | * | 7/1988 | Bossard et al. ............. 361/231 |
| 5,730,149 A | * | 3/1998 | Nakayama et al. ......... 600/573 |
| 5,854,617 A | * | 12/1998 | Lee et al. .................... 345/102 |
| 5,883,934 A | * | 3/1999 | Umeda ........................ 378/64 |
| 5,952,639 A | * | 9/1999 | Ohki et al. .................. 235/379 |
| 5,995,949 A | * | 11/1999 | Morioka et al. ............. 705/43 |
| 6,198,212 B1 | | 3/2001 | Kim et al. |
| 6,771,075 B1 | | 8/2004 | Aiki et al. |
| 2003/0011958 A1 | | 1/2003 | Aiki et al. |

FOREIGN PATENT DOCUMENTS

| | | | | |
|---|---|---|---|---|
| CN | 2230019 Y | | 6/1996 | |
| CN | 1241113 A | | 1/2000 | |
| DE | 3442798 A1 | | 5/1986 | |
| JP | 405266298 A | * | 10/1993 | ................. 235/379 |
| JP | 10-241556 | | 9/1998 | |
| JP | 10-258115 | | 9/1998 | |
| JP | 11-316550 A | | 11/1999 | |
| JP | 2002-095731 A | | 4/2002 | |
| JP | 02002102327 A | * | 4/2002 | |

OTHER PUBLICATIONS

Nishikawa, K. et al., The Effect of Positive and Negative Ions on Air Purification, Summaries of Lectures of Fundamentals and Materials Society of the institute of Electrical Engineers of Japan, pp. 229-234, (2000).

(Continued)

Primary Examiner—Brian Sircus
Assistant Examiner—Boris Benenson
(74) Attorney, Agent, or Firm—Birch, Stewart, Kolasch & Birch, LLP (57) ABSTRACT

A display device includes a display panel and an ion generator for generating positive ions and negative ions. The display device kills microorganisms or decomposes and removes harmful organic substances (e.g., sources of odor or environmental hormones), which exist either on the screen or in the air surrounding the display device, by utilizing the action of the positive and negative ions.

27 Claims, 11 Drawing Sheets

OTHER PUBLICATIONS

Nojima, H. et al., Air Purification Effect of Cluster Ions Generated by Plasma Discharge at Atmospheric Pressure, Summaries and Lectures at 10th Intelligent Material Sumposium, pp. 56-57, (2001).

Nishikawa, K. et al, Air Purification Effect of Positively and Negatively Charged Ions Generated by Discharge Plasma at Atmospheric Pressure, Jpn.J.Appl.Phys., vol. 40, pp L835-L837, (2001).

* cited by examiner

DISPLAY DEVICE INCLUDING ION GENERATOR AND ELECTRONIC APPLIANCE

BACKGROUND OF THE INVENTION

1. Field of the Invention

The present invention relates to a display device and an electronic appliance.

2. Description of the Related Art

Various types of flat-panel displays (FPDs), including liquid crystal displays (LCDs), plasma display panels (PDPs) and electroluminescence (EL) displays, have been researched and developed vigorously since early 1990s. Display devices of these types are much more space-saving than old-fashioned ones, and have rapidly been expanding their applications in audiovisual, office automation, medical imaging and numerous other types of information providing appliances for use in not just homes and offices but also public facilities such as hospitals, restaurants and hotels.

Also, interactive electronic appliances, such as automatic teller machines (ATMs) and electronic guidance systems including a touch panel display, have been popularized recently in those public facilities. An electronic appliance of this type prompts the user to input information responsive to a question displayed thereon or displays information in response to the question that has been input by the user.

Meanwhile, buildings of today are often designed so as to have a highly airtight and thermally insulating structure. Those buildings can certainly shut the heat or the cold off the internal environment but might possibly cause a pollution of the internal air environment unless ventilated or air-conditioned appropriately. Should the internal air environment be polluted with harmful contaminants floating in the indoor air (including microorganisms and odor-emitting organic substances), the human health could be seriously affected by those contaminants, thus potentially causing a rise in the number of allergic patients or asthmatics. Under the circumstances such as these, an increasing number of people should need a device of removing those detrimental contaminants from the indoor air to lead a healthy and comfortable life. Naturally, it is even more pressing to satisfy those needs in sickrooms, diagnosis rooms and operation rooms of hospital facilities among other things.

To meet those needs, air-conditioning systems with a special function, such as air purifiers, have been developed. An air-conditioning system of that type absorbs the air with those contaminants from inside the room or the storeroom and removes those contaminants by getting them adsorbed into, or decomposed by, various sorts of filters. However, such air-conditioning systems require regular maintenance (e.g., filter exchange) because those systems are often operated all day long or at least for a rather long time. In addition, the performance of those air-conditioning systems is not fully satisfactory yet due to the insufficient quality of currently available filters.

Thus, to overcome these problems, air-conditioning systems of the type increasing the ion concentration in the air by using an ion generator (or ionizer) have also been put on the market. However, those ion-generating, air-conditioning systems currently available can generate negative ions only. Such air-conditioning systems may relax the user to a certain degree but should be almost ineffective in removing floating bacteria from the air, for example.

Japanese Laid-Open Publication No. 11-316550 discloses a display device with an air purifying function. However, that display device can just gather dust from the air and cannot remove the floating bacteria from the air, either.

None of the existent display devices or electronic appliances including display devices (such as ATMs and personal computers) has ever been equipped with the function of protecting the user's health. For example, when a display device is used on a medical spot, it is not a rare case at all to watch somebody there disinfect the display screen of the device with alcohol. However, such a custom not just needs manual hygienic maintenance on the display device but may also cause defects in the display device.

SUMMARY OF THE INVENTION

In order to overcome the problems described above, preferred embodiments of the present invention provide a display device and an electronic appliance with the function of safeguarding the user's health against harmful substances (e.g., air-purifying or sterilizing (or disinfecting) function).

A display device according to a preferred embodiment of the present invention preferably includes a display panel and an ion generator for generating positive ions and negative ions. The positive and negative ions are preferably cluster ions. The display device according to this preferred embodiment of the present invention kills microorganisms or decomposes and removes harmful organic substances (e.g., sources of odor or environmental hormones), which exist either on the screen or in the air surrounding the display device, by utilizing the action of the positive and negative ions. As used herein, the "microorganisms" includes bacteria (i.e., viable cells), fungi and viruses. To kill those microorganisms will sometimes be referred to herein as "to sterilize" or "to disinfect".

In one preferred embodiment of the present invention, the positive ions preferably include $H^+(H_2O)_m$ (where m is an arbitrary natural number), the negative ions preferably include $O_2^-(H_2O)_n$ (where n is also an arbitrary natural number), and the positive and negative ions preferably react with each other to produce $H_2O_2$ (i.e., hydrogen peroxide molecules) or an OH radical (which will be sometimes denoted herein as ".OH").

In another preferred embodiment, the ion generator preferably generates the positive and negative ions by ionizing water in an atmosphere.

In this particular preferred embodiment, the ion generator preferably ionizes the water in the atmosphere by discharge. The discharge may be an RF induction plasma discharge.

More specifically, the positive ions preferably include a cluster of oxygen molecule ions, and the negative ions also preferably include a cluster of oxygen molecule ions. The cluster of oxygen molecule ions may be generated by producing a corona discharge in the air, for example.

In still another preferred embodiment, the positive and negative ions are preferably supplied onto a screen of the display panel. Alternatively or additionally, the positive and negative ions are preferably supplied toward the head of a person who is using the display device. That is to say, the positive and negative ions may be supplied both onto the screen of the display panel and toward the user's head.

In yet another preferred embodiment, the display device may further include a mechanism for producing a gas flow such that the positive and negative ions are transported on the gas flow. The gas flow producing mechanism may be either a fan or a mechanism that utilizes convection of the heat that has been generated from a heat source. If the display device itself includes a heat-dissipating fan as in a PDP or a projector, there is no need to add the ion transporting fan but the heat-dissipating fan may be used instead.

In yet another preferred embodiment, the ion generator may be turned ON or OFF synchronously with a turn ON or OFF of the display panel. Alternatively, the ion generator may also be turned ON or OFF asynchronously with a turn ON or OFF of the display panel. As another alternative, the ion generator may switch its modes of operation from a first operation mode, in which the ion generator is turned ON or OFF synchronously with the turn ON or OFF of the display panel, into a second operation mode, in which the ion generator is turned ON or OFF asynchronously with the turn ON or OFF of the display panel, or vice versa.

In yet another preferred embodiment, the display device may further include an environment analyzer for performing a quantitative analysis on the atmosphere. In that case, the display panel may show results of the analysis that have been output from the environment analyzer. Alternatively, the display device may further include an indicator to show the results of the analysis thereon.

In yet another preferred embodiment, the ion generator preferably generates the positive and negative ions at a variable ratio.

In this particular preferred embodiment, the ion generator may operate in a refresh mode to generate the negative ions in a number greater than that of the positive ions. In that case, while the ion generator is operating in the refresh mode, the display panel may present an environmental video thereon.

In yet another preferred embodiment, the display panel may be selected from the group consisting of a liquid crystal display panel, a plasma display panel and an EL display panel.

An electronic appliance according to a preferred embodiment of the present invention preferably includes: a display panel; a processor, which includes a circuit that supplies the display panel with data to be displayed on the panel; and an ion generator for generating positive ions and negative ions. The ion generator does not always form an integral part of the display panel.

In one preferred embodiment of the present invention, the positive ions preferably include $H^+(H_2O)_m$ (where m is an arbitrary natural number), the negative ions preferably include $O_2^-(H_2O)_n$ (where n is also an arbitrary natural number), and the positive and negative ions preferably react with each other to produce $H_2O_2$ or an OH radical.

In another preferred embodiment, the ion generator preferably generates the positive and negative ions by ionizing water in an atmosphere.

In this particular preferred embodiment, the ion generator may ionize the water in the atmosphere by discharge. The discharge may be an RF induction plasma discharge, for example.

In another preferred embodiment, the positive ions may include a cluster of oxygen molecule ions, and the negative ions may also include a cluster of oxygen molecule ions. The cluster of oxygen molecule ions may be generated by producing a corona discharge in the air, for example.

In still another preferred embodiment, the positive and negative ions are preferably supplied onto a screen of the display panel. Alternatively or additionally, the positive and negative ions may be supplied toward the head of a person who is using the electronic appliance. That is to say, the positive and negative ions may be supplied both onto the screen of the display panel and toward the user's head.

In yet another preferred embodiment, the appliance may further include a mechanism for producing a gas flow. In that case, the positive and negative ions are preferably transported on the gas flow.

In this particular preferred embodiment, the appliance preferably further includes a housing to store the processor and the ion generator therein, and the gas flow producing mechanism is preferably also provided inside the housing.

More specifically, the gas flow producing mechanism may be either a fan or a mechanism that utilizes convection of the heat that has been generated from a heat source. The fan may also be used to dissipate the heat from the processor.

In yet another preferred embodiment, the appliance may further include an input device that allows the user to input information to the electronic appliance. In that case, the positive and negative ions are also preferably supplied to the input device. In a preferred embodiment, the input device may be a touch panel that forms an integral part of the display panel.

The electronic appliance including the ion generator may include no display device. For example, the positive and negative ions may be supplied to a glass window or a semi-transparent solar cell, not the display panel. Alternatively, the positive and negative ions may also be supplied to an input device that allows the user to input information either manually with his or her fingers tapped on it or orally with his or her mouth brought closer to it (e.g., the input device of an electronic appliance to be provided in a public place, in particular). In that case, the air surrounding the electronic appliance or the surface of the input device can be purified (i.e., sterilized or deodorized).

Other features, elements, processes, steps, characteristics and advantages of the present invention will become more apparent from the following detailed description of preferred embodiments of the present invention with reference to the attached drawings.

DETAILED DESCRIPTION OF PREFERRED EMBODIMENTS

Hereinafter, the structure and functions of a display device according to preferred embodiments of the present invention and those of an electronic appliance including such a display device will be described with reference to the accompanying drawings. It should be noted, however, that the present invention is in no way limited to the following specific preferred embodiments.

Figure 1:
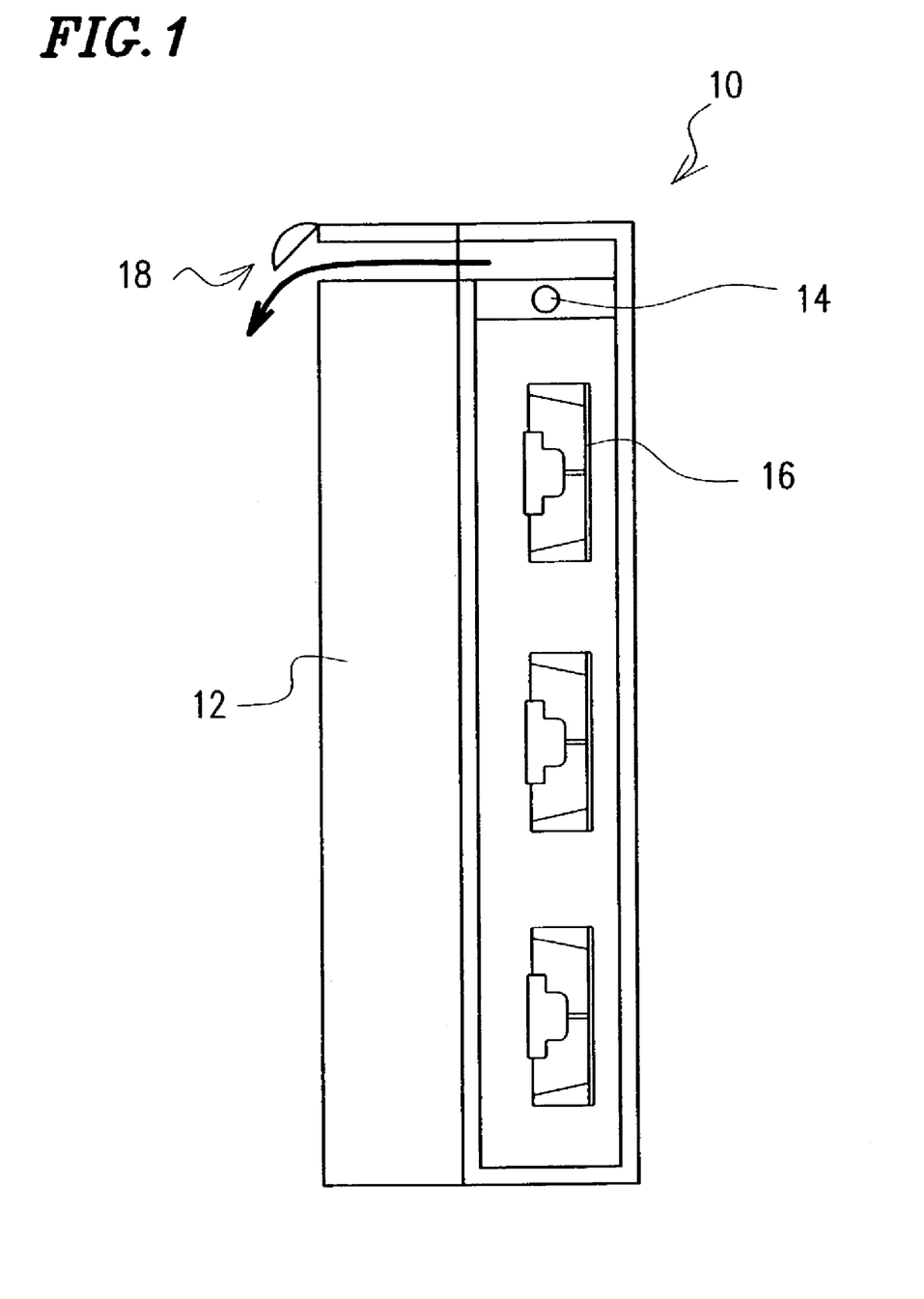
FIG. 1 is a cross-sectional view schematically illustrating a display device 10 according to a specific preferred embodiment of the present invention.

FIG. 1 is a cross-sectional view schematically illustrating the structure of a display device 10 with an ion generator according to a preferred embodiment of the present invention.

As shown in FIG. 1, the display device 10 includes a display panel 12, an ion generator 14 and fans 16. The display panel 12 may be a PDP, for example, and the fans 16 may be heat-dissipating fans for the PDP, for example. The ion generator 14 generates positive ions and negative ions, which are transported on a gas flow, produced by the fans 16, toward the screen of the display panel 12 by way of a nozzle 18. Depending on the size of the display device 10, for example, a portion of the gas flow that has been produced by the fans 16 may be exhausted through the back of the display device 10. In that case, the cluster ions that have been generated by the ion generator 14 are also preferably exhausted on the gas flow. Optionally, multiple ion generators 14 may be provided or the structure of defining the exhaust path may be added. Also, even while the display device 10 is not operating, only the ion generator 14 (and the fans 16) may be activated.

Hereinafter, the structure and operation of the ion generator, which can be used effectively in a display device according to a preferred embodiment of the present invention and an electronic appliance including such a display device, will be described. The ion generator to be preferably used in this preferred embodiment is disclosed in Japanese Patent Application No. 2001-148809, which was filed by the applicant of the present application, Nojima et al., Summaries of Lectures at 10$^{th}$ Intelligent Material Symposium, pp. 56–57, Mar. 15, 2001, and Nishikawa et al., Summaries of Lectures of Fundamentals and Materials Society of the Institute of Electrical Engineers of Japan, pp. 229–234, 2000.

Figure 2:
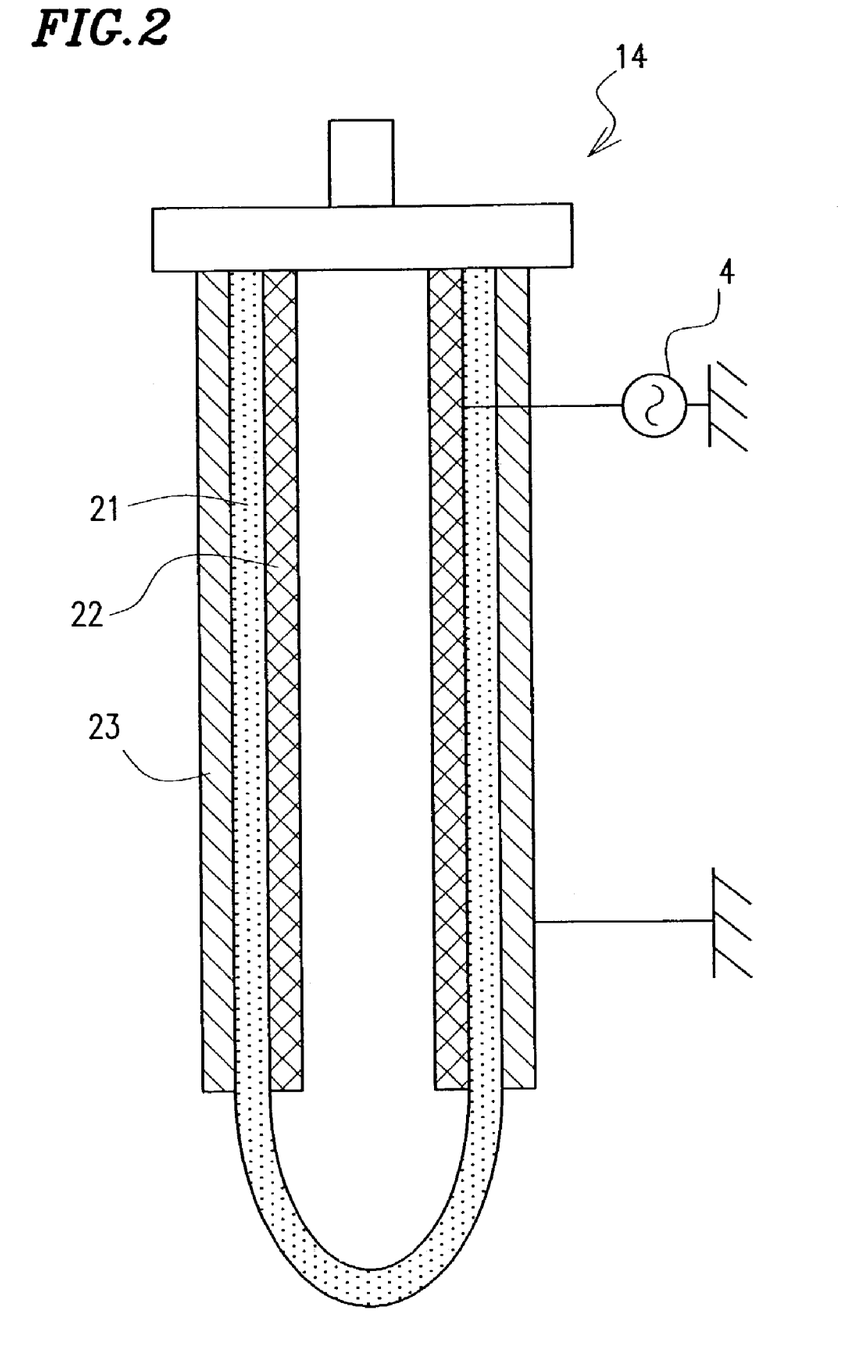
FIG. 2 schematically illustrates the structure of an ion generator that can be used effectively in a display device and an electronic appliance according to a preferred embodiment of the present invention.

FIG. 2 is a cross-sectional view schematically illustrating a structure of the ion generator 14. As shown in FIG. 2, the ion generator 14 includes a glass tube 21, a ground electrode 23 and an application electrode 22. The glass tube 21 is a cylindrical dielectric body with a closed end. The ground electrode 23 is provided on the outer surface of the glass tube 21, while the application electrode 22 is provided on the inner surface of the glass tube 21. An RF generator 4 is connected to the application electrode 22.

The glass tube 21 may be made of Pyrex™ glass with a thickness of about 1 mm, for example. The ground electrode 23 and application electrode 22 are electrodes with a huge number of through holes, which may be meshed sheets of stainless steel SUS304, for example.

With the ground electrode 23 grounded, an AC voltage of about 1 kV to about 3 kV is applied from the RF generator 4 to the application electrode 22 at a frequency on the orders of several to several tens kilohertz. When such a high AC voltage is applied to the application electrode 22, a strong electric field is generated at the end of the meshed ground electrode 23. As a result, a plasma discharge is produced by the ground electrode 23 and water molecules (and oxygen molecules) in the air are ionized, thereby generating positive ions and negative ions.

When an AC voltage having an effective value of about 1.1 kV or about 1.4 kV was applied at a frequency of about 15 kHz, approximately 200,000 to 400,000 positive and negative ions were counted per cubic centimeter at a location that was about 20 cm away from the outer surface of the glass tube 21. The ion concentrations were measured with an aerial ion counter No. 83–1001B produced by Dan Science Corp. Also, these results (and the results of the experiments to be described later) were obtained on small ions having a mobility of about 1 cm$^2$/sec or more. The more distant from the outer surface of the glass tube 21, the lower the ion concentration measured was.

Figure 3A:
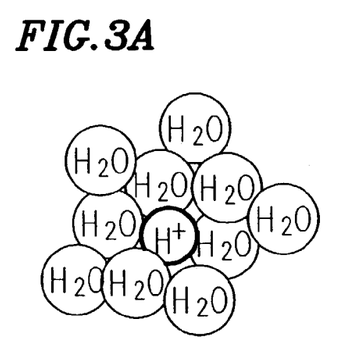
FIGS. 3A and 3B schematically illustrate the structure of cluster ions that are generated by the ion generator.
Figure 3B:
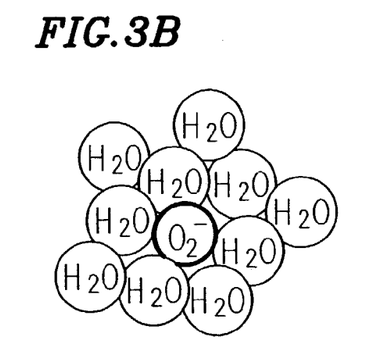

The hydrogen ions (H$^+$), which have been generated by the ionization of water molecules in the air as a result of the plasma discharge, are clustered together with the water molecules in the air as shown in FIG. 3A due to the solvation energy, thereby forming positive cluster ions having a composition represented by H$^+$(H$_2$O)$_m$, where m is an arbitrary natural number. On the other hand, the oxygen ions (O$_2^-$), which have been generated by the ionization of oxygen molecules or water molecules in the air as a result of the plasma discharge, are clustered together with the water molecules in the air as shown in FIG. 3B due to the solvation energy, thereby forming negative cluster ions having a composition represented by O$_2^-$(H$_2$O)$_n$, where n is also an arbitrary natural number.

These positive and negative cluster ions perform sterilization or disinfection (and the decomposition of harmful organic substances) by the following mechanism. These actions are not realized either by positive cluster ions alone or by negative cluster ions alone but realized only when the cluster ions of the two polarities coexist. Also, these actions are most remarkable when the number of positive cluster ions is approximately equal to that of negative cluster ions.

Figure 4:
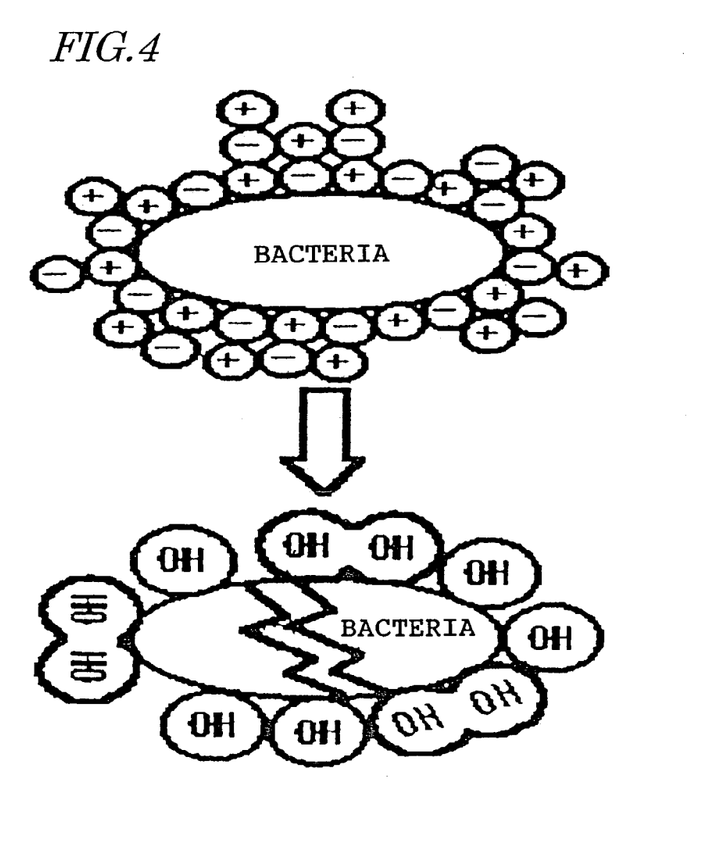
FIG. 4 schematically shows the sterilizing action of positive and negative cluster ions.

As shown in FIG. 4, the positive and negative ions, which have been emitted onto the screen of the display panel and into a living space, surround the bacteria that are floating over the screen and in the indoor air. The positive and negative cluster ions cause chemical reactions as represented by the following Formulae (1) through (3) on the surface of the bacteria, thereby producing hydrogen peroxide (H$_2$O$_2$) or a hydroxide radical (.OH) as an active species:

$$H^+(H_2O)_m + O_2^-(H_2O)_n \rightarrow \cdot OH + \tfrac{1}{2}O_2 + (m+n)H_2O \quad (1)$$

$$H^+(H_2O)_m + H^+(H_2O)_{m'} + O_2^-(H_2O)_n + O_2^-(H_2O)_{n'} \rightarrow 2\cdot OH + O_2 + (m+m'+n+n')H_2O \quad (2)$$

$$H^+(H_2O)_m + H^+(H_2O)_{m'} + O_2^-(H_2O)_n + O_2^-(H_2O)_{n'} \rightarrow H_2O_2 + O_2 + (m+m'+n+n')H_2O \quad (3)$$

where m, m', n and n' are arbitrary natural numbers. Sterilization (or disinfection) is realized by the decomposing action of this active species.

Figure 5:
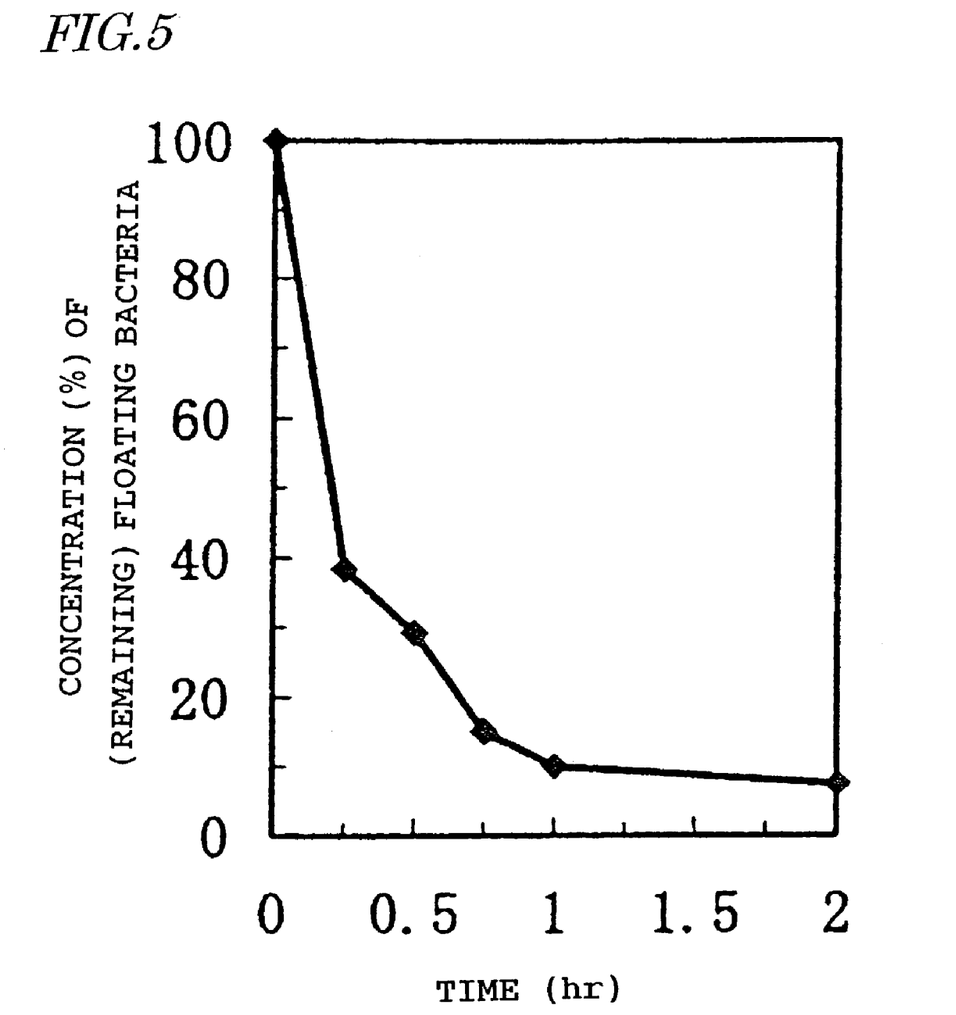
FIG. 5 is a graph showing how effectively the positive and negative cluster ions can kill the floating bacteria.

If the positive and negative cluster ions, generated by the ion generator 14, are sufficiently exhausted by the fans provided for the display device, the bacteria in the air can be killed as shown in FIG. 5. As can be seen from the results shown in FIG. 5, about 90% of the bacteria can be killed in an hour. Similar results were also obtained on bacteria (e.g., *Escherichia coli*). The concentration of the floating bacteria was measured with an RCS Air Sampler (produced by Biotest AG, Germany) in an atmosphere having a temperature of about 25° C. and a relative humidity of about 42%.

The positive and negative cluster ions can not only kill the bacteria but also decompose and detoxify various sorts of harmful or toxic organic substances existing in a living space as shown in the following Table 1:

TABLE 1

| Harmful substance | Main emission sources | Chemical reaction formula | Components of product | | | |
|---|---|---|---|---|---|---|
| | | | $H_2O$ | $CO_2$ | N | $O_2$ |
| Ammonia | urine, pets, sweat, tobacco smoke | $2NH_3 + 6OH \rightarrow N_2 + 6H_2O$ | ◯ | | ◯ | |
| Acetaldehyde | garbage, tobacco smoke | $CH_3CHO + 6OH + O_2 \rightarrow 2CO_2 + 5H_2O$ | ◯ | ◯ | | |
| Acetic acid | garbage, vinegar, tobacco smoke | $CH_3COOH + 4OH + O_2 \rightarrow 2CO_2 + 4H_2O$ | ◯ | ◯ | | |
| Methane gas | gas fuel, garbage, fart | $CH_4 + 4OH + O_2 \rightarrow CO_2 + 4H_2O$ | ◯ | ◯ | | |
| Carbon monoxide | fuel smoke | $CO + 2OH \rightarrow CO_2 + H_2O$ | ◯ | ◯ | | |
| Nitrogene monoxide | exhaust gas, tobacco smoke | $2NO + 4OH \rightarrow N_2 + 2O_2 + 2H_2O$ | ◯ | | ◯ | ◯ |
| Formaldehyde | new or reconstructed building walls | $HCHO + 4OH \rightarrow CO_2 + 3H_2O$ | ◯ | ◯ | | |

It should be noted that the effects of the cluster ions change depending on the specific type of the poisonous gas to get rid of. Thus, some harmful substances may not be decomposed completely.

Figure 6:
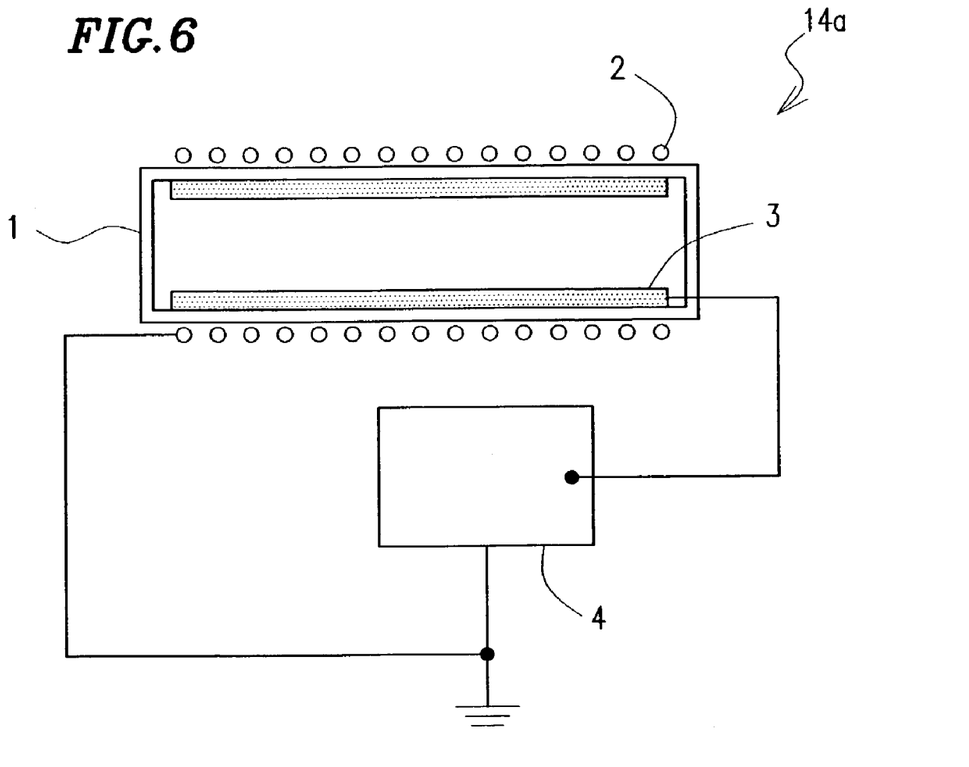
FIG. 6 schematically illustrates the structure of another ion generator that can be used effectively in a display device and an electronic appliance according to a preferred embodiment of the present invention.

FIG. 6 schematically illustrates the cross-sectional structure of an ion generator 14a according to another specific preferred embodiment of the present invention. As shown in FIG. 6, the ion generator 14a includes: a glass tube 1, which is a cylindrical dielectric body; a ground electrode 2 provided on the outer surface of the glass tube 1; and an application electrode 3 provided on the inner surface of the glass tube 1.

The glass tube 1 may be a Pyrex™ tube with an inside diameter of about 10 mm, a thickness of about 1.3 mm and a length of about 150 mm. The ground electrode 2 may be a meshed sheet of stainless steel SUS304 with a wire diameter of about 0.23 mm, a number of openings of 30 and a length of about 100 mm. The application electrode 3 may be a plate of stainless steel SUS304 with a thickness of about 0.8 mm and a length of about 80 mm.

An RF generator 4 is connected between the ground electrode 2 and the application electrode 3. By getting an AC voltage applied from the RF generator 4 to the application electrode 3, a plasma discharge is produced from the ground electrode 2. As a result, positive and negative cluster ions are generated in a similar manner.

The ion concentration at a location that was about 10 cm away from the outer surface of the ion generator 14a was measured with a variable effective voltage of about 1.3 kV to about 1.8 kV applied from the RF generator 4 to the application electrode 3 at a frequency of about 22 kHz. A fan was disposed on the opposite side of the ion generator 14a, i.e., so as to face the ion counter with the ion generator 14a interposed between them. The ion concentration was measured with a gas flow blown at a wind speed of about 3 m/sec.

While no voltage was applied to the application electrode 3, the ion concentration of the positive ions and that of the negative ions each measured about 300 ions per $cm^3$. However, once the AC voltage applied exceeded about 1.52 kV, the generation of the ions from the ion generator 14a was definitely recognized. For example, when a voltage of about 1.6 kV was applied, the ion count was approximately 10,000 ions per cubic centimeter or more. And when a voltage of about 1.8 kV was applied, the ion count was approximately 300,000 ions per cubic centimeter or more. Thus, it was confirmed that the higher the voltage applied, the higher the ion concentration. The present inventors also discovered that the ion concentration should be at least about 10,000 ions per cubic centimeter to kill the floating bacteria sufficiently.

Figure 7:
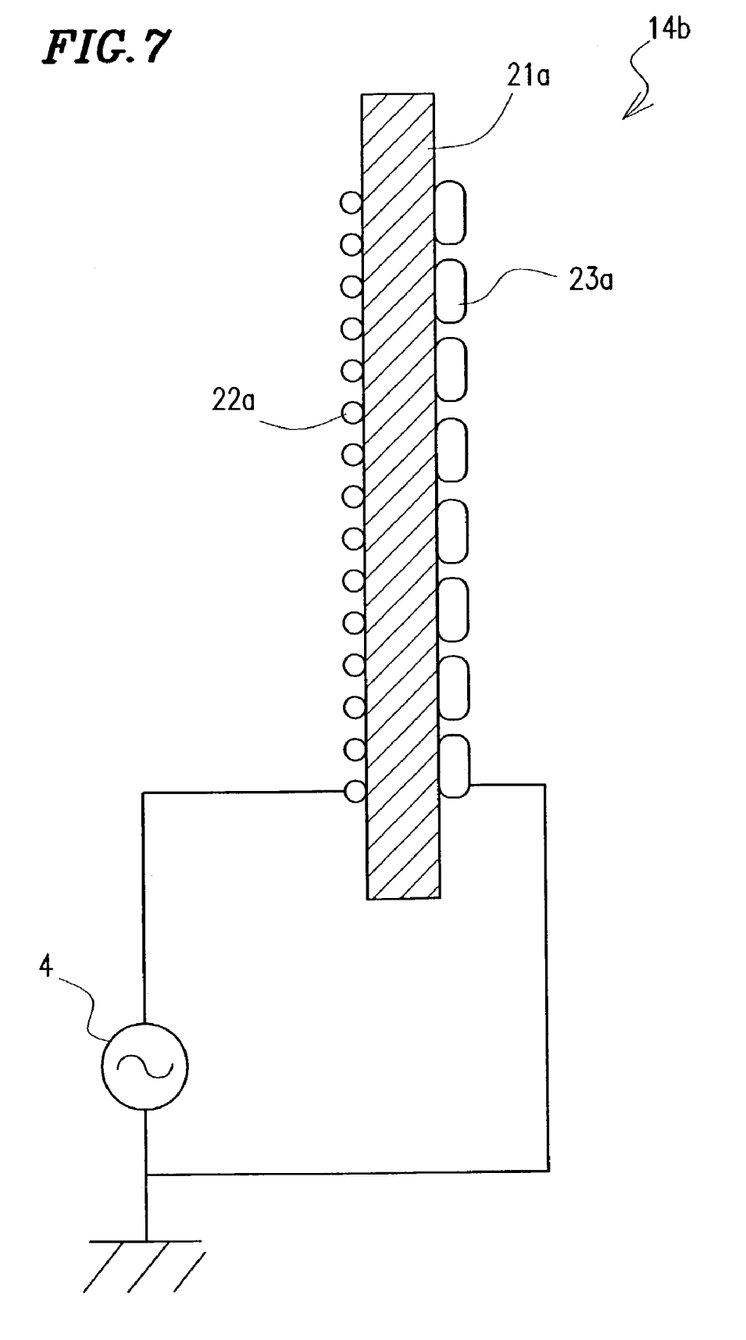
FIG. 7 schematically illustrates the structure of still another ion generator that can be used effectively in a display device and an electronic appliance according to a preferred embodiment of the present invention.

An ion generator 14b such as that shown in FIG. 7 may also be used. As shown in FIG. 7, the ion generator 14b includes: a glass plate 21a, which is a plate-shaped dielectric body; and a ground electrode 23a and an application electrode 22a, which are disposed so as to face each other with the glass plate 21a interposed between them. The glass plate 21a may be a Pyrex™ plate with a thickness of about 3 mm, while the ground electrode 23a and the application electrode 22a may be meshed sheets of stainless steel SUS304. When an AC voltage is applied from an RF generator 4 to the application electrode 22a with the ground electrode 23a grounded, a plasma discharge is produced from the ground electrode 23a. As a result, positive and negative cluster ions can be generated in a similar manner.

For example, when an AC voltage with an effective value of about 3 kV was applied at a frequency of about 20 kHz, approximately 60,000 to 70,000 positive ions and a similar number of negative ions were counted simultaneously per cubic centimeter at a location that was about 10 mm away from the surface of the glass plate 21a of this ion generator 14b.

The ion generator 14b uses the plate-shaped dielectric body (i.e., the glass plate 21a). Accordingly, compared to the ion generator 14 shown in FIG. 2 or the ion generator 14a shown in FIG. 6, the ground and application electrodes 23a and 22a can be formed and maintained more easily. In addition, the ground and application electrodes 23a and 22a can keep a closer contact with the dielectric body, thus increasing the reliability of the ion generator 14b.

The ion generators 14, 14a and 14b described above may have their sizes and operating conditions (including applied voltage and/or frequency) adjusted according to the sizes and applications of the display device and electronic appliance. For example, in a large-sized display device such as a PDP, a projector or a CRT, the cluster ions may be constantly exhausted and diffused by fans. Then, not just the surface and its neighboring regions of the display screen but also the air surrounding the display device can be purified sufficiently.

Also, a number of display devices for personal computers or a number of liquid crystal TVs are often arranged and used within a single living space. In that case, even if the air purifying function of each display device is relatively low, the air in the living space can still be purified sufficiently as a whole.

As described above, display devices and electronic appliances according to various preferred embodiments of the present invention can purify the display screen, its neighboring regions and the surrounding air. As a result, the display device can be kept clean and the surrounding air can be purified. Accordingly, the present invention is particularly effectively applicable to display devices and electronic appliances for use in highly hygiene-sensitive places such as hospitals that should be as free from bacteria and other harmful substances as possible.

In addition, the cluster ions generated by the ion generator can not just purify the air but also remove static electricity. As is often the case with conventional CRTs, the surface of a display panel gets electrified easily, thus adsorbing dust or chemical substances thereto frequently due to the static electricity generated. However, if the cluster ions are supplied onto the display panel, then that unwanted static electricity, as well as the organic substances floating around, is removable from the display screen. As a result, the display screen can be free from those organic substances, which would otherwise be deposited thereon easily, and can be kept very clean. Consequently, the display device just needs a simple maintenance and rarely causes defects if ever.

Also, it is known that negative ions have effects of relaxing human beings. Accordingly, when the user feels such needs, he or she can make the ion generator generate the positive and negative ions at a different ratio by adjusting the frequency of the voltage applied.

Figure 8:
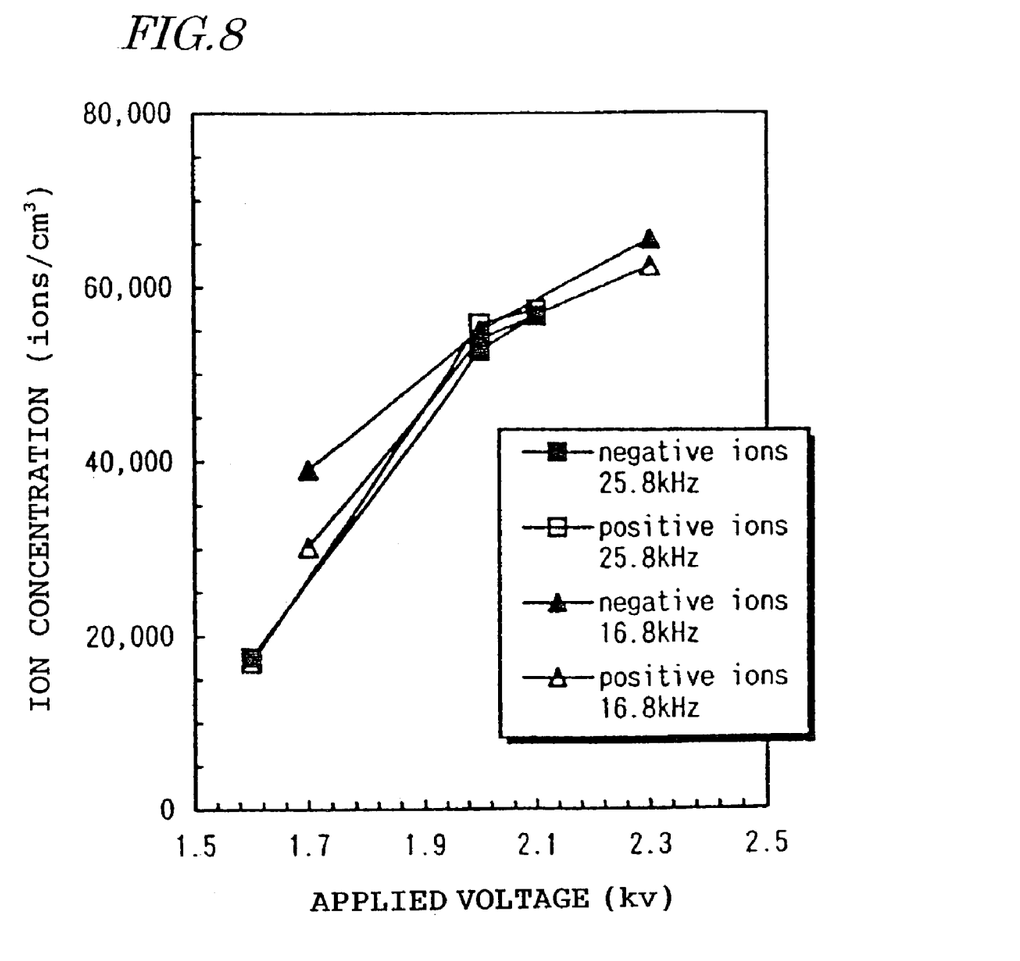
FIG. 8 is a graph showing differences in concentration between the positive and negative ions that have been generated by the ion generator.

FIG. 8 shows how the resultant concentrations of positive and negative ions, which had been generated by the cylindrical ion generator shown in FIG. 2 or 6, changed with the voltage applied at two frequencies of about 16.8 kHz and about 25.8 kHz.

As can be clearly seen from the results shown in FIG. 8, if a voltage having an effective value of about 2 kV or more was applied, then the number of positive ions counted was almost equal to that of negative ions counted irrespective of the frequency at which the voltage was applied. On the other hand, if a voltage having an effective value of less than about 2 kV was applied at the frequency of about 16.8 kHz, then the number of negative ions counted was greater than that of positive ions counted.

By utilizing this phenomenon, the ion generator may be operated in such a manner as to generate the positive and negative ions in almost the same numbers when the air purification effects are preferred. However, when not so much air purification effects as relaxation effects are needed, the ion generator may be operated to generate the negative ions in a greater number than the positive ions.

These modes of operation may be switched either arbitrarily by the user or automatically depending on the results of analysis that has been performed by an environment analyzer. The environment analyzer may be provided for the display device or electronic appliance to carry out a quantitative analysis on the atmospheric gas. Optionally, the results of the quantitative analysis performed by the environment analyzer may be shown on the display device. To do so, an indicator showing those results may be separately provided for the display device. Also, if the ion generator is provided for an electronic appliance such as a personal computer, then the computer may receive the results of analysis that has been carried out by the separately-provided analyzer and transmitted from the analyzer either wirelessly or through a communication line, and may control the operation of the ion generator based on those results.

It should be noted that the ion generator might generate ozone. If the amount of ozone generated exceeds a critical value, human bodies may be seriously affected by that ozone. To avoid the unwanted situation, an ozone sensor is preferably provided near the ion generator or near the exhaust ports of the display device and the ion generator is preferably controlled so as not to generate ozone in an amount exceeding the critical value (see Japanese Patent Application No. 2001-148809, for example).

Some display device (e.g., a display device for a personal computer) may be kept ON for a rather long time even while the user is inputting no commands to its processor. In that situation, the ion generator may be switched into the refresh mode, and at the same time, the display device may start replaying an environmental video thereon. Optionally, the environmental video (such as pictures of forests or a special video) may be accompanied with environmental or relaxing music or sounds (e.g., stream murmur or birds' songs). It is naturally possible to reproduce any other video, music or sound that was registered by the user in advance. The modes of operation of the display device may be switched either synchronously or asynchronously with switching of the ion generator. Alternatively, the user may switch the synchronous mode into the asynchronous mode or vice versa. Any of various known electric circuits may be used to switch these modes of operation.

Hereinafter, specific embodiments of a display device including the ion generator and those of an electronic appliance including such a display device will be described.

Figure 9A:
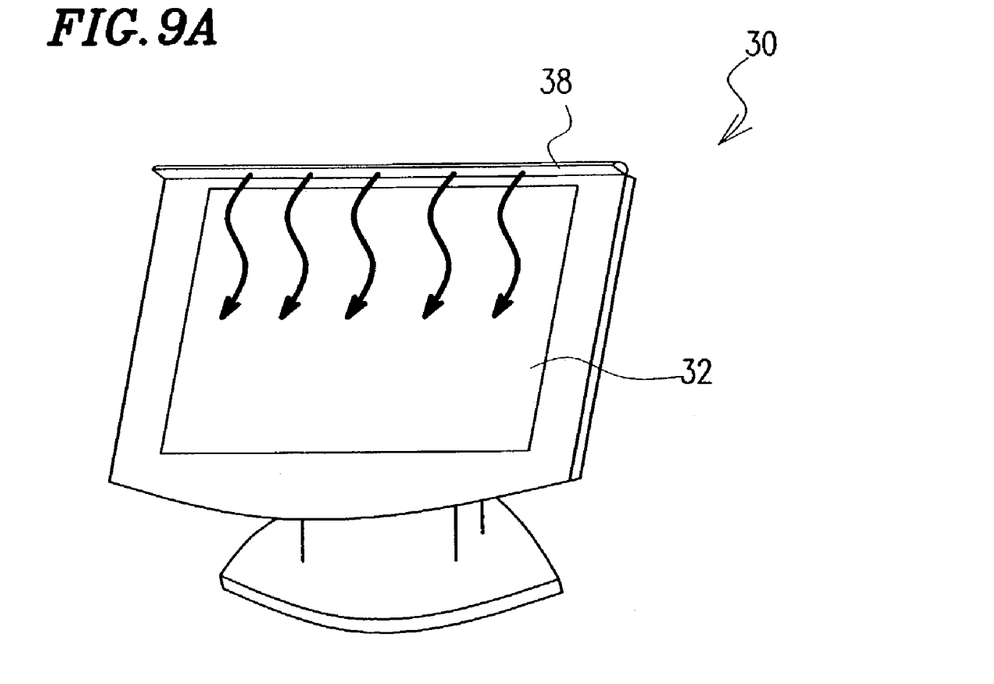
FIGS. 9A and 9B schematically illustrate two liquid crystal display devices according to specific preferred embodiments of the present invention.
Figure 9B:
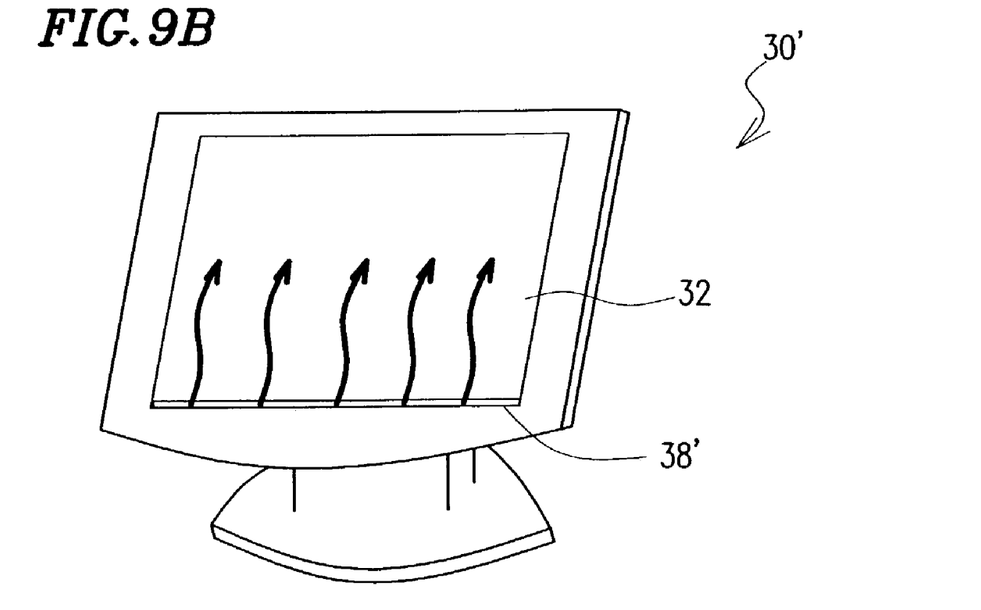

FIGS. 9A and 9B schematically illustrate two specific embodiments of liquid crystal display devices 30 and 30'.

The liquid crystal display device 30 shown in FIG. 9A includes an LCD panel 32 and the ion generator (not shown). In this display device 30, positive and negative cluster ions, generated by the ion generator, are supplied through a nozzle 38 onto the display screen by using a gas flow that has been produced due to the heat of the backlight in the display panel 32. Naturally, fans may be provided on the back of the LCD panel 32 to get the gas flow blown more strongly.

On the other hand, the liquid crystal display device 30' shown in FIG. 9B includes a slit 38' at the bottom of the display screen such that the positive and negative cluster ions are supplied through the slit 38' onto the screen. In this specific embodiment, the cluster ions are diffused toward the top of the screen on a gas flow that has been produced by the heat of the display screen.

The ion generator is naturally applicable for use in not just these liquid crystal display devices but also an organic EL display device, an FED display device and various other display devices. Also, if the ion generator is provided for a liquid crystal display device, the voltage to be applied to the ion generator may be easily generated just by slightly modifying a power supply for its backlight.

Figure 10:
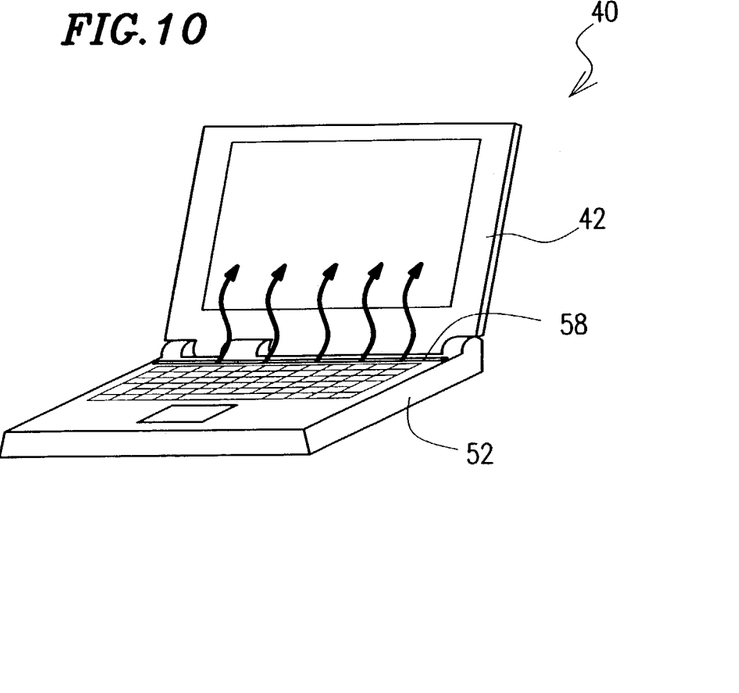
FIG. 10 schematically illustrates a personal computer according to another specific preferred embodiment of the present invention.

FIG. 10 schematically illustrates a notebook personal computer 40 as a specific embodiment of an electronic appliance according to the present invention.

As shown in FIG. 10, the computer 40 includes a display panel (display device) 42 and a processor (i.e., the body of the computer) 52 including a circuit that supplies the data to be displayed on the display panel 42. The ion generator is stored in the housing of the processor 52. In this specific embodiment, the positive and negative cluster ions are supplied through a nozzle 58 onto the display panel 42 by using a gas flow that has been produced by a fan (not shown) inside the processor 52.

Figure 11:
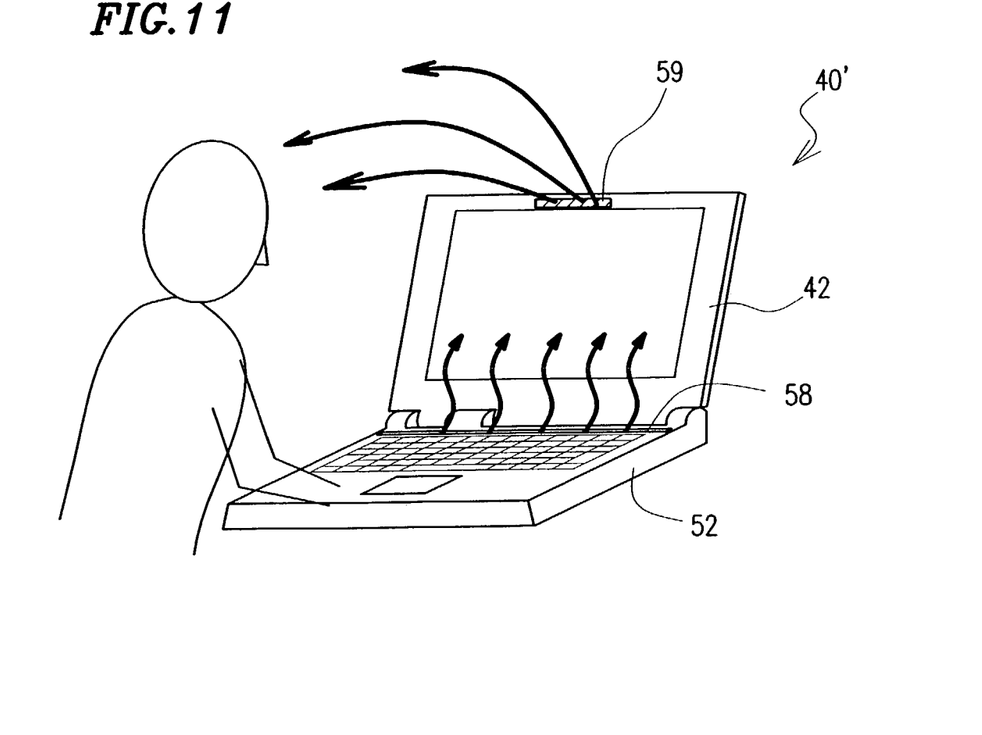
FIG. 11 schematically illustrates another personal computer according to still another specific preferred embodiment of the present invention.

FIG. 11 schematically illustrates another notebook personal computer 40' as another specific embodiment of an electronic appliance according to the present invention. As shown in FIG. 11, the computer 40' includes an ion outlet port 59 at the top of its display panel (display device) 42 such that a gas flow (or wind) of positive and negative cluster ions is blown out forward through the outlet port 59. However, if the gas flow is blown directly against the face of a person who is using this computer 40', the user will feel uncomfortable (e.g., his or her eyes dried abnormally). For that reason, the gas flow is preferably blown in such a direction as supplying the positive and negative cluster ions toward the head of the user. It should be noted that even if those positive and negative cluster ions are blown up toward the head, the ions can go down around the user by themselves and can purify the air surrounding the user effectively as long as the amount of cluster ions supplied is sufficient.

To eject the positive and negative cluster ions from the ion outlet port 59 more effectively, gas flow producers such as fans may be provided additionally. Also, if a sufficient amount of positive and negative cluster ions can be supplied through the ion outlet port 59 onto the display panel 42, the nozzle 58 may be omitted.

Figure 12:
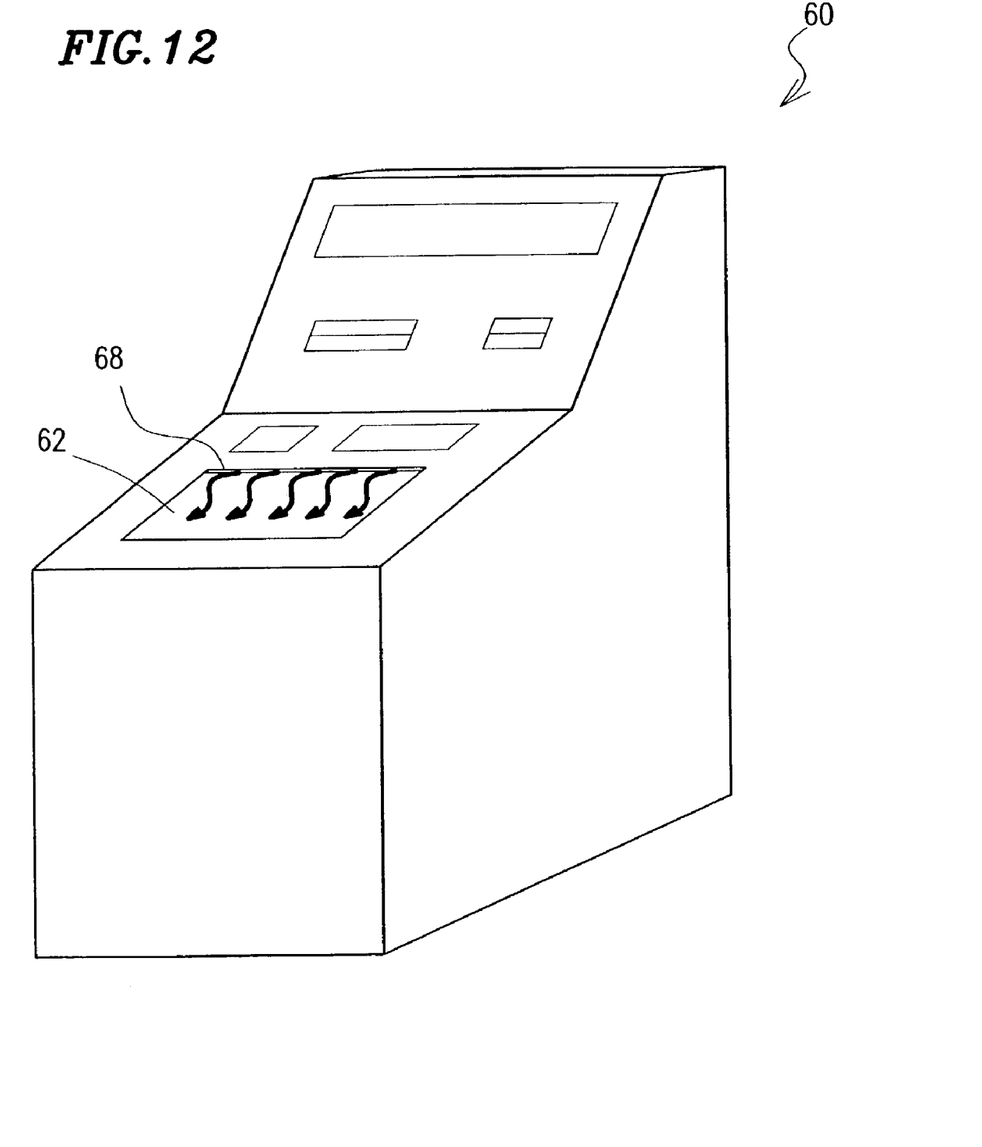
FIG. 12 schematically illustrates an ATM according to yet another specific preferred embodiment of the present invention.

FIG. 12 schematically illustrates an ATM 60 as another specific embodiment of an electronic appliance including the display device (display panel) 62 of the present invention.

The ion generator (not shown) and fans (not shown, either) are provided inside this ATM 60. The positive and negative cluster ions, generated by the ion generator, are supplied through a nozzle 68 onto the display screen. The display device 62 also functions as an input device of a touch panel type. In response to a question displayed on the display device 62, the user inputs required information with the input device that forms an integral part of the display panel 62. Many people directly lay their fingers everyday on an appliance such as the ATM 60. Accordingly, an appliance of this type needs hygienic maintenance more frequently than any other type of appliance. In the prior art, however, such maintenance has been carried out manually. In contrast, in the ATM 60 of this preferred embodiment, the display screen, or the surface of the input device, is always kept clean by the purifying action of the positive and negative cluster ions.

Figure 13:
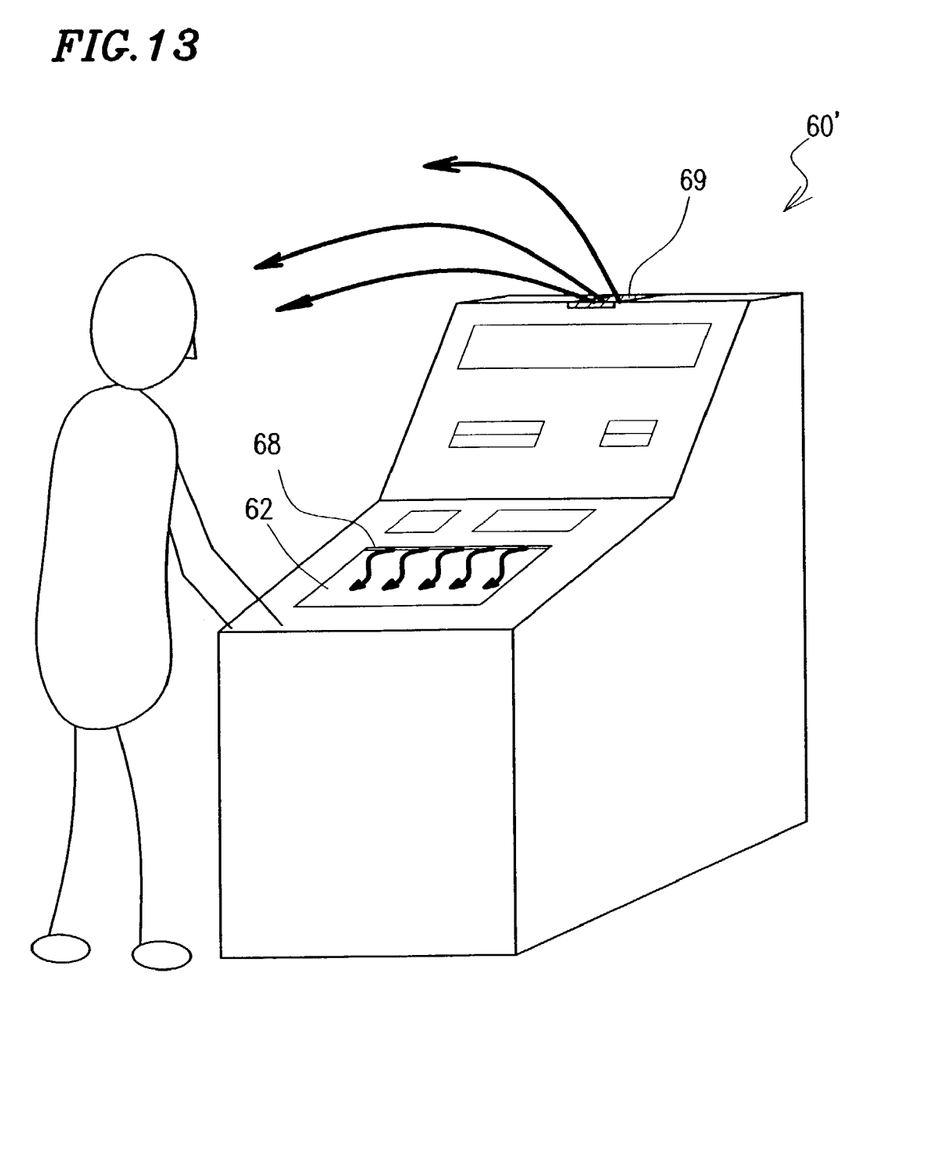
FIG. 13 schematically illustrates another ATM according to yet another specific preferred embodiment of the present invention.

FIG. 13 schematically illustrates another ATM 60' as another specific embodiment of an electronic appliance according to the present invention. As shown in FIG. 13, the ATM 60' includes an ion outlet port 69 at the top of its housing such that a gas flow (or wind) of positive and negative cluster ions is blown out forward through the outlet port 69. However, if the gas flow is blown directly against the face of a person who is using this ATM 60', the user will feel uncomfortable (e.g., his or her eyes dried abnormally). For that reason, the gas flow is preferably blown in such a direction as supplying the positive and negative cluster ions toward the head of the user. It should be noted that even if those positive and negative cluster ions are blown up toward the head, the ions can go down around the user by themselves and can purify the air surrounding him or her effectively as long as the amount of cluster ions supplied is sufficient. The ion outlet port 69 does not have to be provided at the position shown in FIG. 13 but may be shifted to any other position as long as the positive and negative cluster ions can be effectively supplied toward the head of the user.

To eject the positive and negative cluster ions from the ion outlet port 69 more effectively, gas flow producers such as fans may be added. Also, if necessary, an appliance of a big size may include additional ion generator(s). Furthermore, if a sufficient amount of positive and negative cluster ions can be supplied through the ion outlet port 69 onto the display panel 62, the nozzle 68 may be omitted.

An interactive display device has recently been developed as a replacement for the traditional display devices described above and has already been used as an electronic guidance system in public places. The interactive display device includes a touch panel type input device on its display screen, prompts the user to input required information with the input device in response to a question presented on the display screen, and provides his or her desired information through such interactive information exchange. The present invention is also effectively applicable for use in such a display device or an electronic appliance including the display device.

In the preferred embodiments described above, the ion generator generates positive and negative cluster ions by ionizing water molecules in the air through a plasma discharge. Alternatively, an ion generator of the type generating oxygen molecule cluster ions by ionizing oxygen molecules in the air through a corona discharge (e.g., Sun Cluster produced by Nisshin EM Corp.) may also be used.

The ion generator with such a purifying function may be naturally applicable for use in various other types of electronic appliances including no display device. For example, the positive and negative ions may be supplied to a glass window or a semi-transparent solar cell. The ion generator is also effectively applicable for use in the input device of an electronic appliance that allows the user to input information either manually with his or her fingers tapped on it or orally with his or her mouth brought closer to it (e.g., the input device of an electronic appliance to be provided in a public facility, in particular). By providing the ion generator for such an electronic appliance, the air surrounding the electronic appliance and the surface of its input device can be purified (i.e., sterilized or deodorized).

The location(s) and the number of ion generator(s) to be provided for a display device or an electronic appliance are not particularly limited but may be appropriately determined depending on the specific application. Also, the positive and negative cluster ions are preferably supplied onto the display panel and/or toward the head of the user but may be supplied to anywhere else according to the specific application of each device or appliance.

Various preferred embodiments of the present invention described above provide a display device and an electronic appliance that have the function of protecting the user's health such as an air purifying or sterilizing (or disinfecting) function.

A display device or an electronic appliance according to any of various preferred embodiments of the present invention described above can not only purify the display screen and the surrounding air but also remove static electricity from the display screen. Thus, the present invention contributes to providing a clean and comfortable operating environment for not just highly hygiene-sensitive places such as hospitals but also other public facilities used by crowds of people every day, offices and homes. In addition, the present invention can also simplify the maintenance to be done on the display device or electronic appliance.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. A display device comprising:
a display panel; and
an ion generator for generating positive ions and negative ions,
the positive ions include $H^+(H_2O)_m$ (where m is an arbitrary natural number), the negative ions include $O_2^-(H_2O)_n$ (where n is also an arbitrary natural number), and the positive and negative ions react with each other to produce $H_2O_2$ or an OH radical.

2. The device of claim 1, wherein the ion generator generates the positive and negative ions by ionizing water in an atmosphere.

3. The device of claim 2, wherein the ion generator ionizes the water in the atmosphere by discharge.

4. The device of claim 1, wherein the positive ions include a cluster of oxygen molecule ions, and the negative ions also include a cluster of oxygen molecule ions.

5. A display device comprising:
a display panel; and
an ion generator for generating positive ions and negative ions, the positive and negative ions are supplied onto a screen of the display panel.

6. The device of claim 5, wherein the positive and negative ions are supplied toward the head of a person who is using the display device.

7. The device of claim 5, further comprising a mechanism for producing a gas flow,
wherein the positive and negative ions are transported on the gas flow.

8. The device of claim 7, wherein the gas flow producing mechanism includes a fan.

9. The device of claim 5, wherein the ion generator is turned ON or OFF synchronously with a turn ON or OFF of the display panel.

10. The device of claim 5, wherein the ion generator is turned ON or OFF asynchronously with a turn ON or OFF of the display panel.

11. The device of claim 5, wherein the ion generator switches its modes of operation from a first operation mode, in which the ion generator is turned ON or OFF synchronously with the turn ON or OFF of the display panel, into a second operation mode, in which the ion generator is turned ON or OFF asynchronously with the turn ON or OFF of the display panel.

12. The device of claim 5, wherein the ion generator generates the positive and negative ions at a variable ratio.

13. The device of claim 1, wherein the display panel is selected from the group consisting of a liquid crystal display panel, a plasma display panel and an EL display panel.

14. A display device comprising:
a display panel; and
an ion generator for generating positive ions and negative ions further comprising an environment analyzer for performing a quantitative analysis on the atmosphere,
wherein the display panel shows results of the analysis that have been output from the environment analyzer.

15. The device of claim 14, further comprising an indicator to show the results of the analysis thereon.

16. A display device comprising:
a display panel; and
an ion generator for generating positive ions and negative ions the ion generator is able to operate in a refresh mode to generate the negative ions in a number greater than that of the positive ions, and
wherein while the ion generator is operating in the refresh mode, the display panel displays an environmental video thereon.

17. An electronic appliance comprising:
a display panel;
a processor, which includes a circuit that supplies the display panel with data to be displayed on the panel; and
an ion generator for generating positive ions and negative ions wherein the positive ions include a cluster of oxygen molecule ions, and the negative ions also include a cluster of oxygen molecule ions.

18. The appliance of claim 17, wherein the positive ions include $H^+(H_2O)_m$ (where m is an arbitrary natural number), the negative ions include $O_2^-(H_2O)_n$ (where n is also an arbitrary natural number), and the positive and negative ions react with each other to produce $H_2O_2$ or an OH radical.

19. The appliance of claim 17, wherein the ion generator generates the positive and negative ions by ionizing water in an atmosphere.

20. The appliance of claim 19, wherein the ion generator ionizes the water in the atmosphere by discharge.

21. An electronic appliance comprising:
a display panel;
a processor, which includes a circuit that supplies the display panel with data to be displayed on the panel; and
an ion generator for generating positive ions and negative ions wherein the positive and negative ions are supplied onto a screen of the display panel.

22. The appliance of claim 21, wherein the positive and negative ions are supplied toward the head of a person who is using the electronic appliance.

23. The appliance of claim 21, further comprising a mechanism for producing a gas flow,
wherein the positive and negative ions are transported on the gas flow.

24. The appliance of claim 23, further comprising a housing to store the processor and the ion generator therein, wherein the gas flow producing mechanism is also provided inside the housing.

25. The appliance of claim 23, wherein the gas flow producing mechanism includes a fan.

26. The appliance of claim 23, further comprising an input device that allows the user to input information to the electronic appliance,
wherein the positive and negative ions are also supplied to the input device.

27. The appliance of claim 26, wherein the input device is a touch panel that forms an integral part of the display panel.

* * * * *